(12) United States Patent
Lavigne et al.

(10) Patent No.: US 12,296,479 B2
(45) Date of Patent: May 13, 2025

(54) ADMITTANCE MODE CONTROL SYSTEM AND METHOD FOR ROBOTIC ARM

(71) Applicant: KINOVA INC., Boisbriand (CA)

(72) Inventors: Eric Lavigne, Boisbriand (CA);
Sebastien Messier, Boisbriand (CA);
Sebastien Boisvert, Boisbriand (CA);
Jean-Luc Bouchard, Boisbriand (CA)

(73) Assignee: KINOVA INC., Boisbriand (CA)

( * ) Notice: Subject to any disclaimer, the term of this patent is extended or adjusted under 35 U.S.C. 154(b) by 444 days.

(21) Appl. No.: 16/756,880

(22) PCT Filed: Oct. 19, 2018

(86) PCT No.: PCT/CA2018/051321
§ 371 (c)(1),
(2) Date: Apr. 17, 2020

(87) PCT Pub. No.: WO2019/075572
PCT Pub. Date: Apr. 25, 2019

(65) Prior Publication Data
US 2021/0197366 A1    Jul. 1, 2021

Related U.S. Application Data

(60) Provisional application No. 62/574,506, filed on Oct. 19, 2017.

(51) Int. Cl.
*B25J 9/16* (2006.01)
*A61B 34/00* (2016.01)
*A61B 34/30* (2016.01)

(52) U.S. Cl.
CPC ............... *B25J 9/161* (2013.01); *A61B 34/30* (2016.02); *A61B 34/70* (2016.02); *B25J 9/1635* (2013.01); *B25J 9/1643* (2013.01)

(58) Field of Classification Search
CPC ........ B25J 9/1674; B25J 9/1643; B25J 9/161; B25J 9/1635; A61B 34/30; A61B 34/70
See application file for complete search history.

(56) References Cited

U.S. PATENT DOCUMENTS

| | | | | |
|---|---|---|---|---|
| 4,531,192 A | * | 7/1985 | Cook | G05B 19/4207 901/42 |
| 4,839,533 A | * | 6/1989 | Aga | H01H 3/022 307/115 |
| 6,212,443 B1 | * | 4/2001 | Nagata | G05B 19/423 700/63 |
| 10,016,900 B1 | * | 7/2018 | Meyer | B25J 9/0084 |

(Continued)

*Primary Examiner* — Stephen Holwerda
(74) *Attorney, Agent, or Firm* — NORTON ROSE FULBRIGHT CANADA LLP

(57) ABSTRACT

An admittance mode control system for a robotic arm includes an admittance switch adapted to be mounted to the robotic arm. A rotary contact connects a control circuitry to the admittance switch. The control circuitry is adapted to be mounted to the robotic arm, rotational degree(s) of freedom being present between the control circuitry and the admittance switch, the control circuitry interpreting signals to filter circuit misconduct from admittance switch activation. The control circuitry is adapted to communicate a request for admittance to a robot driver for the robot driver to convert an operation of the robotic arm into admittance mode.

20 Claims, 4 Drawing Sheets

(56) References Cited

U.S. PATENT DOCUMENTS

| | | | |
|---|---|---|---|
| 2003/0085681 A1* | 5/2003 | Sakamoto | B25J 19/0025 318/568.16 |
| 2007/0013336 A1* | 1/2007 | Nowlin | A61B 34/30 318/568.21 |
| 2007/0120512 A1 | 5/2007 | Albu-Schaffer et al. | |
| 2016/0359707 A1* | 12/2016 | Martin | H04L 27/2601 |
| 2017/0128136 A1 | 5/2017 | Post | |
| 2018/0065252 A1* | 3/2018 | Tabandeh | B25J 9/1694 |

* cited by examiner

ADMITTANCE MODE CONTROL SYSTEM AND METHOD FOR ROBOTIC ARM

CROSS-REFERENCE TO RELATED APPLICATION

The present application claims the priority of U.S. Patent Application No. 62/574,506, filed on Oct. 19, 2018, and incorporated herein by reference.

TECHNICAL FIELD

The present application relates to robotic arms and to control systems and methods thereof.

BACKGROUND OF THE ART

Robotic arms are increasingly used in a number of different applications, from manufacturing, to servicing, and assistive robotics, among numerous possibilities. Serial robotic arms are convenient in that they cover wide working volumes. The instruments at the effector end of robotic arms may be self-operated, or may be connected to a drive mechanism that may control the instruments in different ways, such as adjusting their position and/or orientation, drive the operation of the instrument, etc. The movements of the robotic arms may be fully robotized, or may be operated in an admittance mode, also known as a collaborative mode, in which the robotic arm allows constrained movements to be done as guided by human manipulations. By applying forces to the robotic arm to manipulate it, in such admittance mode, an operator may directly control the position of the robotic arm.

During a medical procedure, the robotic arms are in a fixed or constrained disposition controlled by the operator. The disposition may be ergonomically suitable for the operator, however, it may also interfere with the duties of other personnel in the room. In some instances, an emergency may require personnel to move around, in which instances they may be blocked by the robotic arms. It would therefore be desirable to allow flexibility in the arm position during the procedure.

Existing approaches for admittance mode, also known as hand guidance, are documented but they fail to describe a safety control loop that prevents unwanted movement of the robotic arm in the case of a malfunction of components that would initiate the admittance mode behavior of the robotic arm, or a malfunction of a component part of the robotic arm motorized joint.

SUMMARY

It is an aim of the present disclosure to provide a control system with admittance mode for robotic arms that addresses issues related to the prior art.

It is a further aim of the present disclosure to provide a control method for robotic arm manipulations in an admittance mode that addresses issues related to the prior art.

Therefore, in accordance with a first embodiment of the present disclosure, there is provided an admittance mode control system for a robotic arm comprising: an admittance switch adapted to be mounted to the robotic arm; a rotary contact; control circuitry connected to the admittance switch via the rotary contact, and adapted to be mounted to the robotic arm, at least one rotational degree of freedom being present between the control circuitry and the admittance switch, the control circuitry interpreting signals to filter circuit misconduct from admittance switch activation; and whereby the control circuitry is adapted to communicate a request for admittance to a robot driver for the robot driver to convert an operation of the robotic arm into admittance mode.

Further in accordance with the first embodiment, the control circuitry comprises for instance a single-pole double-throw momentary switch comprising a normally-open pole-throw switch and a normally-closed pole-throw switch.

Still further in accordance with the first embodiment, the admittance switch is for instance configured for actuating the normally-open pole-throw switch and the normally-closed pole-throw switch when actuated.

Still further in accordance with the first embodiment, the control circuitry further comprises for instance a not-or (NOR) gate, wherein the normally-open pole-throw switch and the normally-closed pole-throw switch are coupled to the NOR gate.

Still further in accordance with the first embodiment, the NOR gate is for instance implemented in hardware.

Still further in accordance with the first embodiment, the NOR gate is for instance implemented in software.

Still further in accordance with the first embodiment, the control circuitry comprises for instance voltage level shifters to adjust a voltage of signals of the control circuitry for transmission to a microcontroller controlling operation of the robotic arm.

Still further in accordance with the first embodiment, the microcontroller is for instance included.

Still further in accordance with the first embodiment, the admittance switch is for instance adapted to project from a tubular body of the robotic arm.

Still further in accordance with the first embodiment, the admittance switch is for instance adapted to be located proximate to an effector end of the robotic arm.

In accordance with a second embodiment of the present disclosure, there is provided for instance a method for converting an operation of a robotic arm into admittance mode, the robotic arm of the type having an admittance switch, a rotary contact, and control circuitry connected to the admittance switch via the rotary contact, the method comprising: receiving signals from the rotary contact; interpreting the signals to filter circuit misconduct from admittance switch activation; identifying one of the signals as admittance switch activation; and communicating a request for admittance to a robot driver to convert an operation of the robotic arm into admittance mode.

Further in accordance with the second embodiment, interpreting the signals comprises for instance routing the signals through a single-pole double-throw momentary switch comprising a normally-open pole-throw switch and a normally-closed pole-throw switch.

Still further in accordance with the second embodiment, identifying one of the signals as admittance switch activation occurs for instance responsive to the admittance switch being actuated, thereby actuating the normally-open pole-throw switch and the normally-closed pole-throw switch.

Still further in accordance with the second embodiment, interpreting the signals comprises for instance routing the signals through a not-or (NOR) gate, wherein the normally-open pole-throw switch and the normally-closed pole-throw switch are coupled to the NOR gate.

Still further in accordance with the second embodiment, the NOR gate is for instance implemented in hardware.

Still further in accordance with the second embodiment, the NOR gate is for instance implemented in software.

Still further in accordance with the second embodiment, a voltage of signals of the control circuitry is for instance adjusted prior to transmission to a microcontroller controlling operation of the robotic arm.

Still further in accordance with the second embodiment, the voltage-adjusted signals are for instance transmitted to the microcontroller.

Still further in accordance with the second embodiment, the voltage-adjusted signals comprise for instance the request for admittance.

Still further in accordance with the second embodiment, the voltage-adjusted signal are for instance adjusted to maintain signal integrity of the voltage-adjusted signals.

Still further in accordance with the second embodiment, one of the signals is for instance identified as circuit misconduct, and the robot driver is for instance maintained in a mode of operation.

Still further in accordance with the second embodiment, the operation of the robotic arm is for instance converted into the admittance mode.

Still further in accordance with the second embodiment, the robotic arm is for instance actuated to constrain movements of the robotic arm against human forces, in the admittance mode.

DETAILED DESCRIPTION

Figure 1:
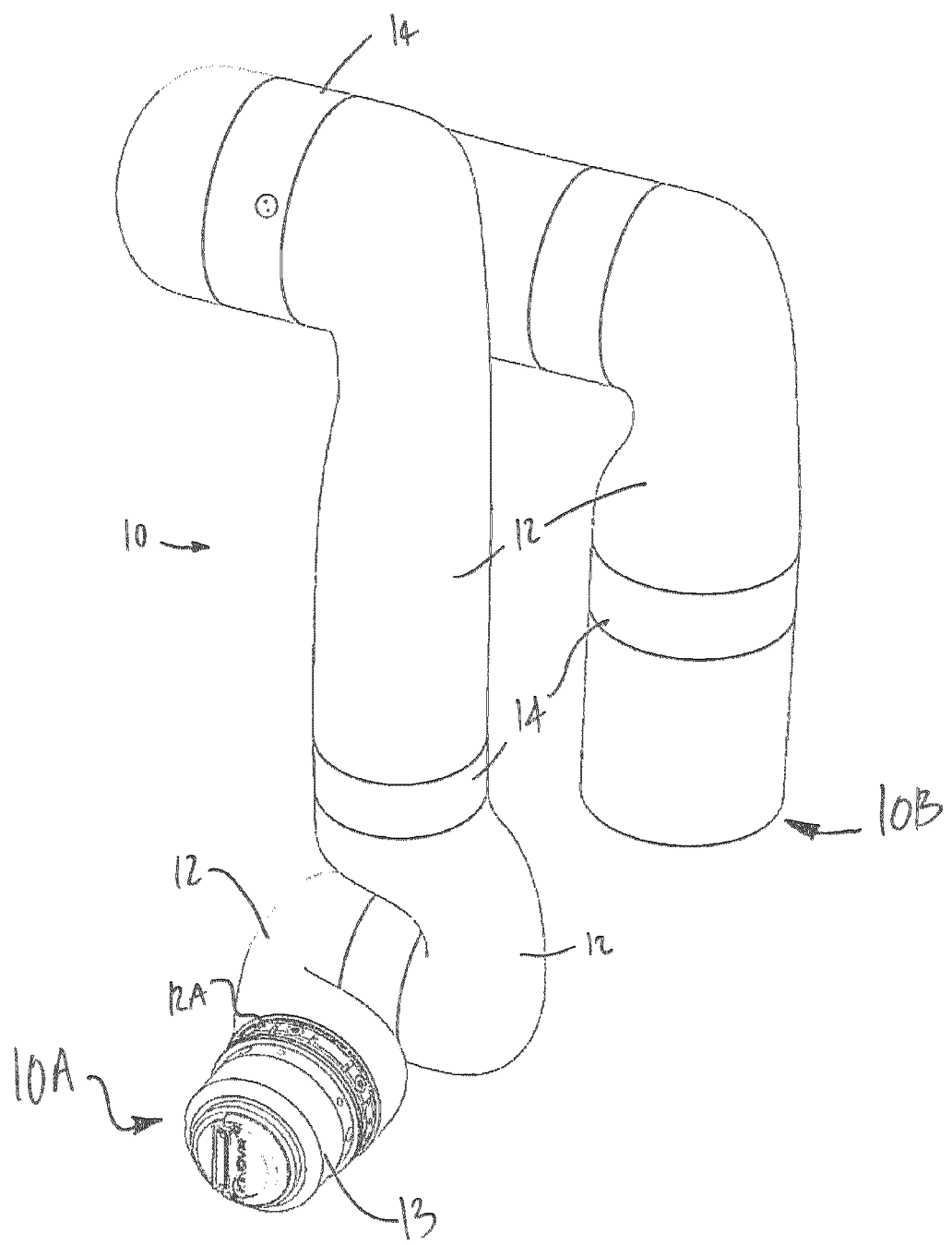
FIG. 1 is a perspective view of an exemplary articulated robotic arm used with the control system of the present disclosure.
Figure 2:
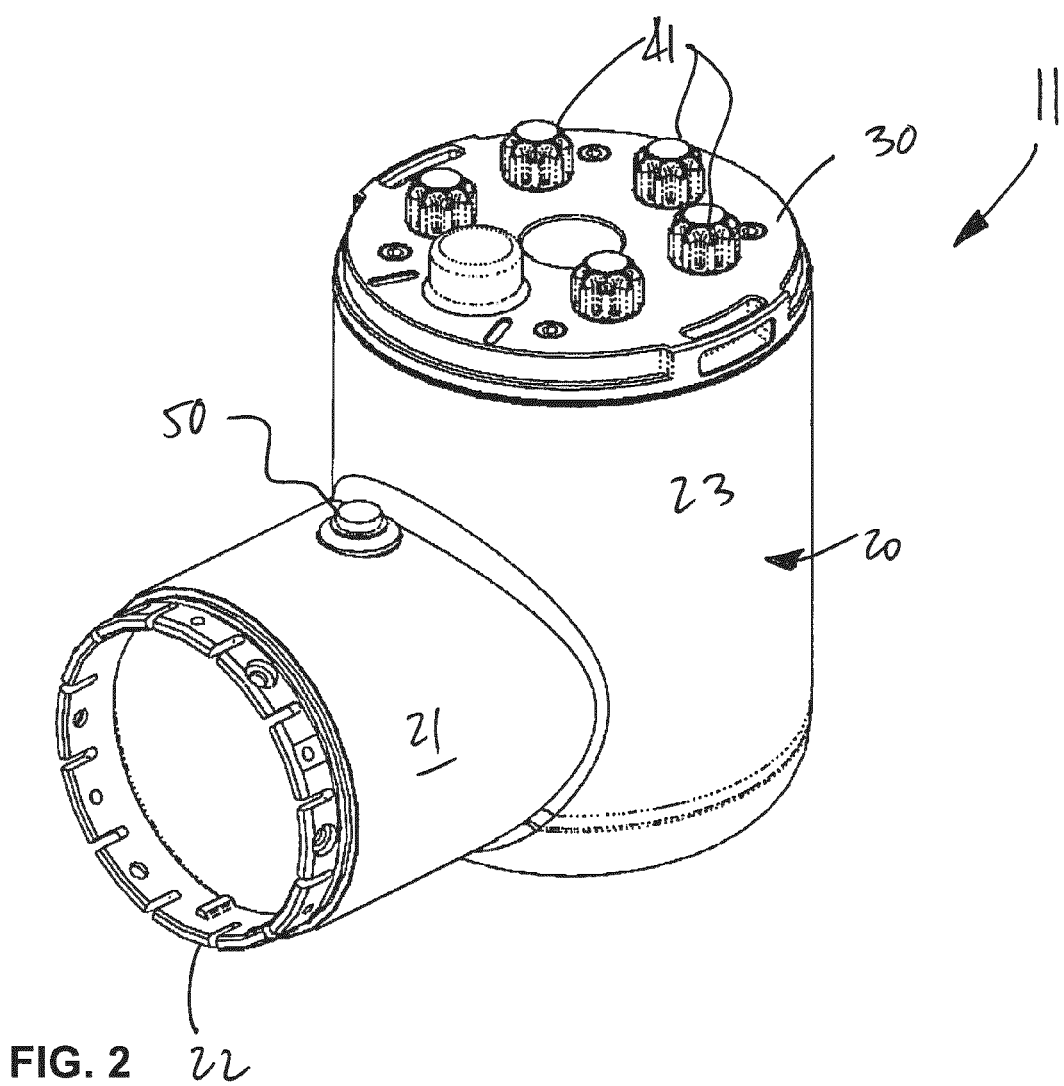
FIG. 2 is a perspective view of an instrument drive mechanism for a robotic arm as in FIG. 1.

Referring to the drawings and more particularly to FIG. 1, a robotic arm that may be used with an admittance mode control system in accordance with the present disclosure is generally shown at 10. The movements of the robotic arm 10 may be fully robotized, or may be operated in an admittance mode, in which the robotic arm allows constrained movements to be done as guided by human manipulations, as allowed and supervised by the admittance mode control system. The admittance mode may also be without robotic constraints, i.e., without the actuation system of the robotic arm 10 imposing constraints/forces on the joints—other than residual forces of friction and magnetic forces that are in the joints of the robotic arm 10. A constraint that may be imposed in the admittance mode is working with a protected volume. For example, the robotic arm 10 may block any movement that would allow the robotic arm 10 to penetrate the working volume or, in another embodiment, any movement that would allow the robotic arm 10 to exit the working volume. By applying forces to the robotic arm to manipulate it, in such admittance mode, an operator may directly control the position of the robotic arm 10. The robotic arm 10 may consequently operate in an admittance mode, and in other modes. Other modes may include an automated mode or automatic mode in which the robotic arm 10 operates autonomously, i.e., without human forces, to performed given maneuvers. Another mode is a lock mode or safety mode, in which all joints of the robotic arm 10 may be locked, to prevent any movement of the robotic arm 10, whether as a result of human forces, accidental environmental forces, etc. The robotic arm 10 is a serial articulated robotic arm, having an effector end 10A and a base end 10B. The effector end 10A is configured to receive thereon an instrument drive mechanism 11, such as shown in FIG. 2, and any appropriate instrument. The base end 10B is configured to be connected to any appropriate structure or mechanism. The base end 10B may be rotatably mounted or not to the structure or mechanism. By way of non-exhaustive example, the base end 10B may be mounted to a frame, to a cart, to a robot docking station, for instance in an operating room. The base end 10B could also be in another type of setting, such as an assembly line. Although a serial robotic arm is shown the joint arrangement of the robotic arm 10 may be found in other types of robots, including parallel manipulators.

Referring to FIG. 2, the instrument drive mechanism 11, occasionally referred to herein as mechanism 11 for simplicity, is shown as for supporting and driving an instrument. The mechanism 11 may interface an instrument to the robotic arm 10, or may have a different configuration and be an instrument, the instrument being known as an end effector. However, for simplicity, reference is made herein to an instrument, but this encompasses tools and/or end effectors of all types, such as gripping mechanism or gripper, anamorphic hand, endoscope, catheter, and tooling heads such as drills, saws, etc.

Referring back to FIG. 1, by way of a non-limitative example, the robotic arm 10 may have a series of links 12 (a.k.a., shells), interconnected by motorized joint units 13, with protective sleeves 14 at the junction between adjacent links 12:

The links 12 define the majority of the outer surface of the robotic arm 10. The links 12 also have a structural function in that they form the skeleton of the robotic arm 10 (i.e., an outer shell skeleton), by supporting the motorized joint units 13 and tools at the effector end 10A, with loads supported by the tools, in addition to supporting the weight of the robotic arm 10 itself. Wires and electronic components may be concealed into the links 12, by internal routing. The open ends of the links 12 may each have a connector 12A for interconnection of links 12 with the motorized joint units 13, and with the mechanism 11.

The motorized joint units 13 interconnect adjacent links 12, in such a way that a rotational degree of actuation is provided between adjacent links 12. According to an embodiment, the motorized joint unit 13 shown in FIG. 1 is connected to the mechanism 11 of FIG. 2. The motorized joint units 13 may also form part of the structure of the robotic arm 10, as they interconnect adjacent links 12.

The protective sleeves 14 shield the junction between pairs of adjacent links 12, e.g., in a water, fluid and particle resistant manner. The protective sleeves 14 may form a continuous fastener-less surface from one link 12 to another, as explained hereinafter. Although not shown to avoid interference, another protective sleeve 14 may be between at the junction of the mechanism 11 with the effector end 10A of the robotic arm 10.

Figure 4:
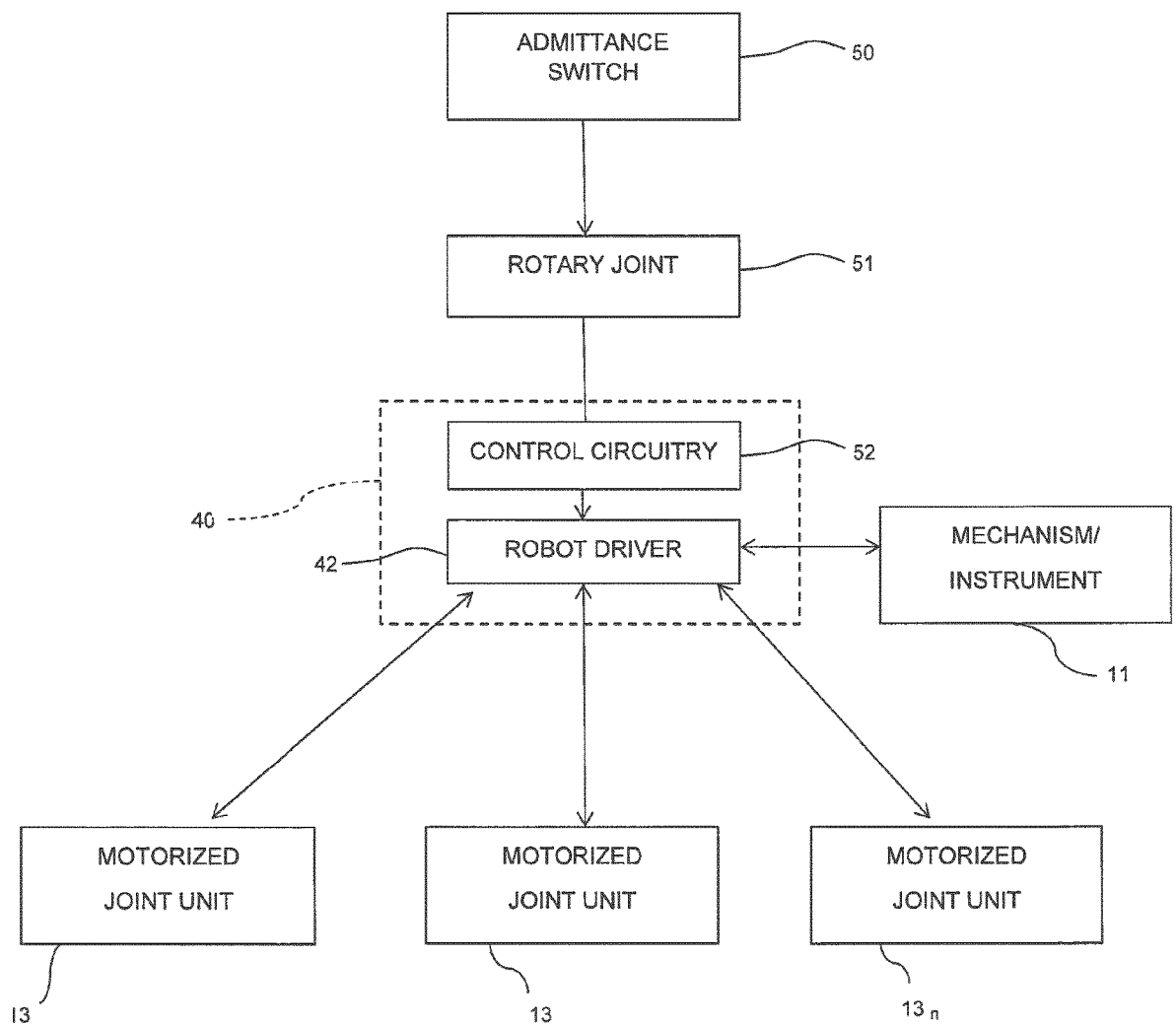
FIG. 4 is a block diagram showing a relation between the admittance mode control system and driver electronics of the articulated robotic arm.

Referring now to FIGS. 2 and 4, the mechanism 11 has an outer shell 20, a top cover 30, a drive system 40 driving outputs 41 and may or may not have the capacity of controlling robotic movements of the articulated robot arm 10, and an admittance switch 50. These components are divided in sub-components but generally form four main groups of the mechanism 11.

The outer shell 20 serves as a structural component of the mechanism 11, by which it is connected to the robotic arm 10. Moreover, the outer shell 20 supports the various components inside the mechanism 11 including the top cover 30, the drive system. The outer shell 20 will also support the weight of the instrument driven by the mechanism 11, and has the admittance switch 50 thereon.

The top cover 30 is the interface between the instrument and the outer shell 20 and drive system. The top cover 30 therefore outputs the various degrees of actuation (DOAs) as explained hereinafter as received from the drive system 40. According to the illustrated embodiment, the top cover 30 may rotate relative to the outer shell 20.

The drive system 40 is tasked with driving the instrument connected to the mechanism 11 via the outputs 41 with the various DOAs provided by the mechanism 11, for instance in accordance with a robotic application or commands, or through user commands. The drive system 40 therefore comprises hardware such as motors to actuate the outputs 41, and also the drive electronics 40' (FIG. 3) to control the movements of the robotic arm 10 and of the mechanism 11.

The admittance switch 50 is part of the admittance mode control system and is used to override the fixed or controlled disposition of the robotic arm 10, to allow manipulations of the robotic arm 10 in admittance mode.

Referring to FIG. 2, the outer shell 20, also known as skin, is shown as having an elbow-shaped tubular body 21, as one possible shape (e.g., tee shape, straight tube, etc). At one end, the tubular body 21 has a connector 22 that is similar to the connector 12A of the exposed link 12 of the robotic arm 10 in FIG. 1. The connectors 12A and 22 may be as described in U.S. Patent Application No. 62/479,841, incorporated herein by reference. Therefore, the outer shell 20 may be connected to the robotic arm 10 by the complementary connection with the motorized joint unit 13 and as covered by the protective sleeve 14, such that an orientation of the mechanism 11 relative to the robotic arm 10 may be controlled by the motorized joint unit 13. This is one among numerous ways by which the outer shell 20 may be connected to a structure. As discussed previously, the mechanism 11 is not necessarily mounted to a robotic arm 10. For example, a flange may be provided at the end of the outer shell 20 for connection to a structure or mechanism.

The outer shell 20 may further include an open-ended receptacle 23. The open-ended receptacle 23 has an open proximal end, while the distal end is generally closed. An interior of the open-ended receptacle 23, i.e., its inner cavity, may open into an interior of the tubular body 21. This forms a continuous passage, notably for internal routing of cables. The outer surface of the outer shell 20 is generally smooth and without disruptions, such as fasteners holes, but with the admittance switch 50 projecting from its surface. Although shown as projecting from the tubular body 21, the admittance switch 50 could be located on other parts of the outer shell 20, such as on the open-ended receptacle 23. Moreover, the admittance switch 50 could also be located in other parts of the robotic arm 10, such as on one of the links 12 at or near the effector end 10A. The location of the admittance switch 50 at the effector end 10A, and on the end effector or mechanism 11 in the illustrated embodiment, is convenient while the arm 10 is in a medical procedure.

The open-ended receptacle 23 accommodates components of the drive system 40 for driving the outputs 41. Some of these components, including hardware components such as motors and gearboxes, and drive electronics 40', may be mounted to the top cover 30 to rotate therewith. The drive electronics 40' may include a printed circuit board (PCB) with appropriate components and processing capacity to drive the robotic arm 10, mechanism 11 and instrument if present. As shown at FIG. 4, the drive electronics 40' may include a robot driver module 42 tasked with controlling the robotic arm 10, mechanism 11 and instrument according to an application or automation process, such as medical procedures, etc. Accordingly, the drive electronics 40' may rotate with the top cover 30 and the instrument on the mechanism 10.

Due to the rotative nature of the mechanism 11, signals between the drive electronics 40' and actuated components of the robotic arm 10, such as the motorized joint units 13, may be through rotary joints. As an example, the admittance switch 50 may be connected to control circuitry 52 in the drive electronics 40' via rotary joint 51. The rotary joint 51 may incorporate a slipring 51A (FIG. 3) and brush contact system or like rotary contact of conductive nature, for electric signals to be communicated from the admittance switch to the control circuitry 52, for the robotic arm 10 to go into admittance mode. The slipring and brush contact system may be subjected to vibrations and misalignment of slipring traces with the brush contacts, leading to a possible misinterpretation of the switch state by the control circuitry 52. Therefore, precautions need to be taken to avoid a false positive signal generated by an unwanted misconduct of the circuitry.

Figure 3:
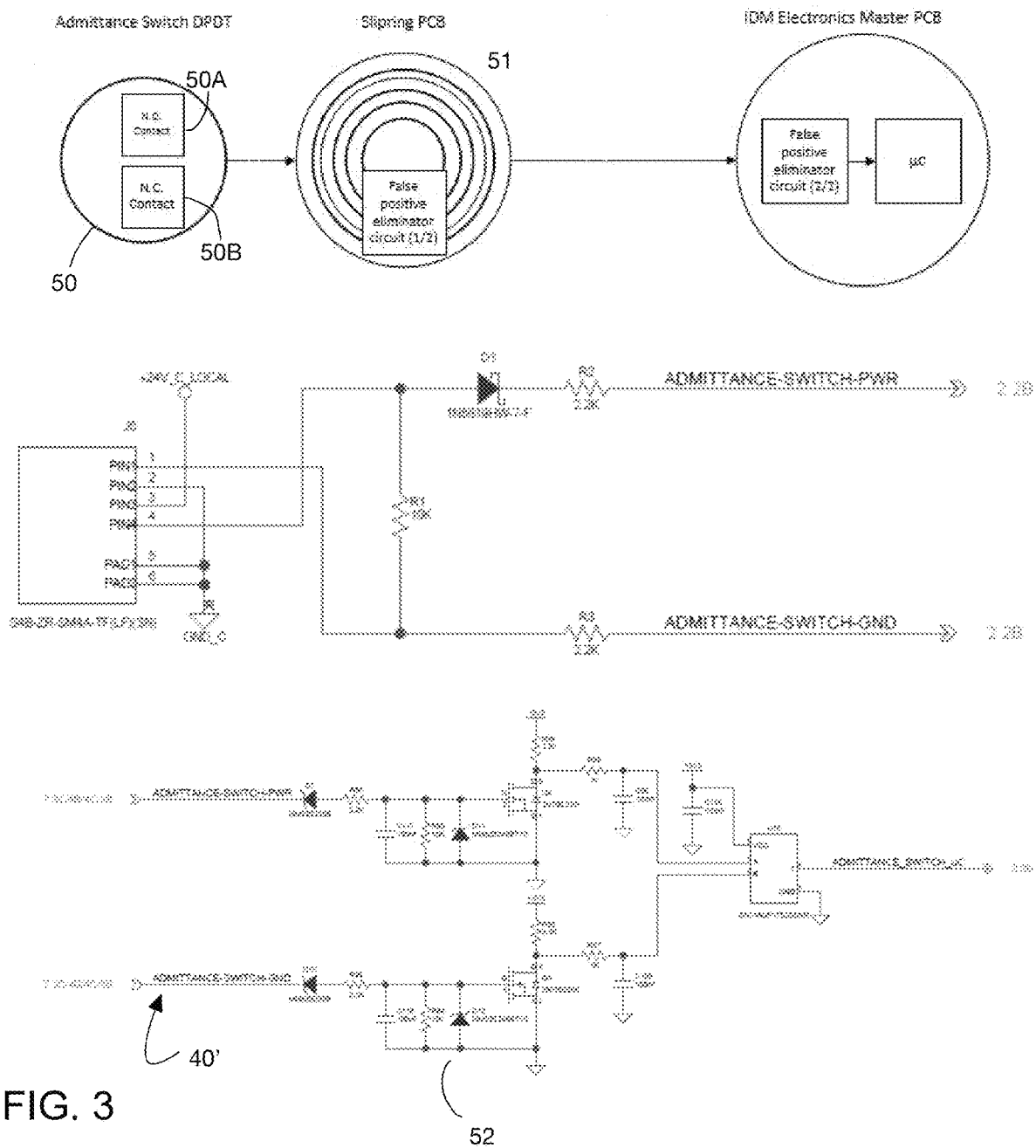
FIG. 3 is a schematic view of the admittance mode control system in accordance with the present disclosure.

For safety reasons, the robotic arm 10 should not activate the admittance mode by accident. Accordingly, the admittance mode control system is provided to prevent the robotic arm 10 to reach the admittance mode by unwanted misconduct of the circuitry. The admittance mode control system includes the admittance switch 50, contacts shown in a simplified format of arrows in FIG. 4, and the control circuitry 52, the latter for instance being part of the drive electronics 40'. Moreover, as also shown in FIG. 3, the circuitry may be mounted onto the drive electronics 40'. The admittance mode control system may also include the rotary joint 51 (with slipring and brush system), though the rotary joint 51 may not be entirely dedicated to communication between the admittance switch 50 and the control circuitry 52. In an embodiment, the admittance switch 50 is retrofitted onto the robotic arm 10, and is connected to the rotary joint 51 already present in the robotic arm 10. The rotary joint 51 may be used for the communication between the robot driver module 42 and the motorized joint units 13.

With reference to FIG. 3, in some embodiments the control circuitry 52 used to implement the admittance mode uses a single-pole double-throw momentary (SPDT MOM) switch, with a first pole-throw switch being normally open (NO) and a second pole-throw switch being normally closed (NC). In other terms, the admittance switch 50 integrates two independent buttons 50A and 50B (a.k.a., contacts) which are opposites, one is normally closed and one is normally open. The contacts 50A and 50B act independently and their combination becomes part of a redundant system, which may be qualified as error free. When the admittance button is pushed or otherwise activated, both the NO and NC contacts are actuated in a mutually exclusive fashion to provide signals to a microcontroller of the control circuitry 52 along first and second circuit paths, respectively, which indicates that the admittance mode is to be activated, whereby the control circuitry 52 allows the robotic arm 10 to follow human manipulations, with or without constraints.

An electronic logic circuit in the control circuitry 52 using the two contacts internal to the admittance switch 50 is used to prevent a false positive from being generated by circuit misconduct. Both contacts internal to the admittance switch 50 are used along with semiconductors and passive components part of the control circuitry 52 in order to perform false positive elimination. The circuitry 52 eliminates the risk of a false positive generated by either a failure of the switch 50 or an unwanted contact between the slipring and the brushes.

Between the switch 50 and the control circuitry 52, there are two contacts each driving an electrical path. Both the NO contact and the NC contact are configured for generating separate and independent control signals, which are routed to a NOR (not-or) logic gate. Each path must generate a specific logic signaling to the logic NOR gate that will only output a true output signal when both its inputs are low. The output of the NOR logic gate is used as the trigger for activating the admittance mode at the microcontroller. In other words, a logic high can only be outputted to a processor of the control circuitry 52 if the switch 50 is pressed. A failure of a contact in the switch 50 or a glitch in the slipring traces may not generate a positive high as shown on the truth table below. It should be noted that the NOR logic gate may be implemented in software or in hardware, as appropriate.

| Switches | Not Pressed | μC1 | μC2 | Pressed | μC1 | μC2 |
|---|---|---|---|---|---|---|
| working | Default | 1 | 1 | Default | 0 | 0 |
| | Adm1Glitch | 0 | 1 | Adm1Glitch | 0 | 0 |
| | Adm2Glitch | 1 | 1 | Adm2Glitch | 0 | 1 |
| N.C. failed open | N.O. not pressed | μC1 | μC2 | N.O. pressed | μC1 | μC2 |
| | Default | 1 | 1 | Default | 0 | 0 |
| | Adm1Glitch | 0 | 1 | Adm1Glitch | 0 | 0 |
| | Adm2Glitch | 1 | 1 | Adm2Glitch | 0 | 1 |
| N.C. failed short | N.O. not pressed | μC1 | μC2 | N.O. pressed | μC1 | μC2 |
| | Default | 1 | 1 | Default | 0 | 1 |
| | Adm1Glitch | 0 | 1 | Adm1Glitch | 0 | 1 |
| | Adm2Glitch | 1 | 1 | Adm2Glitch | 0 | 1 |
| N.O. failed open | N.C. not pressed | μC1 | μC2 | N.C. pressed | μC1 | μC2 |
| | Default | 1 | 1 | Default | 1 | 1 |
| | Adm1Glitch | 0 | 1 | Adm1Glitch | 0 | 1 |
| | Adm2Glitch | 1 | 1 | Adm2Glitch | 1 | 1 |
| N.O. failed short | N.C. not pressed | μC1 | μC2 | N.C. pressed | μC1 | μC2 |
| | Default | 0 | 1 | Default | 0 | 0 |
| | Adm1Glitch | 0 | 1 | Adm1Glitch | 0 | 0 |
| | Adm2Glitch | 0 | 1 | Adm2Glitch | 0 | 1 |

In FIG. 3, the first path is the path of the NO contact, which is connected to a positive voltage source. This contact is the intended path for a true positive of a switch pressed to generate a condition on the microcontroller which enables the admittance mode, which is when the NOR gate inputs are '0' and '0'. If the NO contact fails short, the NC contact is assumed to remain functional, closed and therefore admittance mode is not allowed, since the NOR gate inputs will be '0' and '1'. If the NO contact fails open, the intended path to generate the admittance mode condition can't occur, as the NOR gate inputs will be '1' and '1'. A false positive caused by a misalignment of the slipring in the NO path will be blocked from affecting the NC path by diode D1, and the NOR gate inputs will be '0' and '1'.

The second path is the NC contact which is connected to the electronic ground of the circuit. If the NC contact fails short, the generated condition is the same as if the button wasn't pressed and therefore this condition can't activate the admittance mode, since the NOR gate inputs will be '1' and '1'. A slipring misalignment on the NC contact path will generate the same condition as if the button wasn't pressed. The NOR gate inputs will be '1' and '1', and admittance mode will remain disabled. If the NC contact fails open, a false positive is prevented by pull down resistor R9 and the NOR logic gate inputs will be '1' and '1'.

Voltage level shifters are used to bring the voltage levels used in the circuitry down to logic level signals that can be interpreted by a microcontroller or microprocessor integrated in the control circuitry 52. The circuitry 52 may also contain a mechanism to maintain the signal integrity and avoid bouncing of the signal and minimize the processing required by the system. The robot driver 42 may consequently receive an admittance mode control signal and trigger the admittance mode.

When the admittance mode is active, forces and torques applied by the user on the effector end 10A may be converted into a motion command from the robot driver 42 in a way that the robotic arm 10 responds to user inputs with a configurable dynamic behavior. To do so, torque sensors in each motorized joint unit 13 may communicate the applied torques to the robot driver module 42. Subtracting the effect of gravity using a model of the robotic arm 10, the net forces and torques applied by the user at the end effector can be computed by the robot driver module 42 and the robotic arm 10 may be commanded accordingly.

It should be noted that the particular logic circuit of FIG. 3 is only one example, and false positive rejection can be performed by other means. Additionally, the logic circuit is not necessarily concerned with rejecting false negatives.

The present disclosure also covers a method for converting an operation of a robotic arm such as 10 into admittance mode, the robotic arm 10 of the type having the admittance switch 50, a rotary contact in the rotary joint 51, and the control circuitry 52 connected to the admittance switch 50 via the rotary contact. The method may comprise receiving signals from the rotary contact in the rotary joint 51; interpreting the signals to filter circuit misconduct from admittance switch activation; identifying one of the signals as admittance switch activation; and communicating a request for admittance to the robot driver 42 to convert an operation of the robotic arm 10 into admittance mode.

The invention claimed is:

1. An admittance mode control system for a robotic arm comprising:
   an admittance switch adapted to be mounted to the robotic arm;
   a rotary contact;
   control circuitry connected to the admittance switch via the rotary contact, and adapted to be mounted to the robotic arm, at least one rotational degree of freedom being present between the control circuitry and the admittance switch, the control circuitry interpreting signals to filter circuit misconduct from admittance switch activation during use of the robotic arm for robotic arm manipulations; and
   whereby the control circuitry is adapted to communicate a request for admittance to a robot driver for the robot driver to convert an operation of the robotic arm into admittance mode, the admittance mode enabling constrained movements of the robotic arm as guided by manipulations.

2. The control system of claim 1, wherein the control circuitry comprises a single-pole double-throw momentary switch comprising a normally-open pole-throw switch and a normally-closed pole-throw switch.

3. The control system of claim 2, wherein the admittance switch is configured for actuating the normally-open pole-throw switch and the normally-closed pole-throw switch when actuated.

4. The control system of claim 2, wherein the control circuitry further comprises a not-or (NOR) gate, wherein the normally-open pole-throw switch and the normally-closed pole-throw switch are coupled to the NOR gate.

5. The control system of claim 4, wherein the NOR gate is implemented in hardware.

6. The control system of claim 4, wherein the NOR gate is implemented in software.

7. The control system of claim 1, wherein the control circuitry comprises voltage level shifters to adjust a voltage of signals of the control circuitry for transmission to a microcontroller controlling operation of the robotic arm.

8. The control system of claim 7, further comprising the microcontroller.

9. The control system of claim 1, wherein the admittance switch is adapted to project from a tubular body of the robotic arm.

10. The control system of claim 1, wherein the admittance switch is adapted to be located proximate to an effector end of the robotic arm.

11. A method for converting an operation of a robotic arm into admittance mode, the robotic arm of the type having an admittance switch, a rotary contact, and control circuitry connected to the admittance switch via the rotary contact, the method comprising:
   receiving signals from the rotary contact during use of the robotic arm in a procedure;
   interpreting the signals to filter circuit misconduct from admittance switch activation, the circuit misconduct originating from the rotary contact;
   identifying one of the signals as admittance switch activation; and
   communicating a request for admittance to a robot driver to convert an operation of the robotic arm into admittance mode, the admittance mode enabling constrained movements of the robotic arm as guided by manipulations.

12. The method of claim 11, wherein interpreting the signals comprises routing the signals through a single-pole double-throw momentary switch comprising a normally-open pole-throw switch and a normally-closed pole-throw switch.

13. The method of claim 12, wherein identifying one of the signals as admittance switch activation occurs responsive to the admittance switch being actuated, thereby actuating the normally-open pole-throw switch and the normally-closed pole-throw switch.

14. The method of claim 12, wherein interpreting the signals comprises routing the signals through a not-or (NOR) gate, wherein the normally-open pole-throw switch and the normally-closed pole-throw switch are coupled to the NOR gate.

15. The method of claim 14, wherein the NOR gate is implemented in hardware.

16. The method of claim 14, wherein the NOR gate is implemented in software.

17. The method of claim 11, further comprising adjusting a voltage of signals of the control circuitry prior to transmission to a microcontroller controlling operation of the robotic arm.

18. The method of claim 17, further comprising further adjusting the voltage-adjusted signal to maintain signal integrity of the voltage-adjusted signals.

19. The method of claim 11, further comprising identifying one of the signals as circuit misconduct, and maintaining the robot driver in a mode of operation.

20. The method of claim 11, further comprising converting the operation of the robotic arm into the admittance mode.

\* \* \* \* \*